United States Patent
Guest et al.

(10) Patent No.: US 6,765,666 B1
(45) Date of Patent: Jul. 20, 2004

(54) SYSTEM AND METHOD FOR INSPECTING BUMPED WAFERS

(75) Inventors: Clyde Maxwell Guest, Plano, TX (US); Younes Chtioui, Dallas, TX (US); Rajiv Roy, Plano, TX (US); Charles K. Harris, Dallas, TX (US); Weerakiat Wahawisan, Carrollton, TX (US); Thomas C. Carrington, Plano, TX (US)

(73) Assignee: Semiconductor Technologies & Instruments, Inc., Plano, TX (US)

( * ) Notice: Subject to any disclaimer, the term of this patent is extended or adjusted under 35 U.S.C. 154(b) by 266 days.

(21) Appl. No.: 09/631,509

(22) Filed: Aug. 3, 2000

(51) Int. Cl.⁷ ................................. G01N 21/88
(52) U.S. Cl. ................. 356/237.4; 356/237.5; 382/145; 382/150
(58) Field of Search ............ 356/237.1, 237.2, 356/237.3, 237.4, 237.5; 382/145–151, 276–308

(56) References Cited

U.S. PATENT DOCUMENTS

| | | | |
|---|---|---|---|
| 5,923,430 A | 7/1999 | Worster et al. | 356/394 |
| 5,956,134 A | 9/1999 | Roy et al. | 356/237.5 |
| 6,577,757 B1 * | 6/2003 | DeYong et al. | 382/149 |

FOREIGN PATENT DOCUMENTS

| | | |
|---|---|---|
| EP | 0 959 654 A2 | 11/1999 |
| JP | 07183697 | 7/1995 |
| WO | PCT/JP99/00874 | 2/1999 |

OTHER PUBLICATIONS

PCT Search Report for application PCT/US01/24492.

* cited by examiner

Primary Examiner—Richard A. Rosenberger
Assistant Examiner—Vincent P. Barth
(74) Attorney, Agent, or Firm—Christopher J. Rourk; Akin Gump Strauss Hauer & Feld, LLP

(57) ABSTRACT

A system for inspecting a component, such as a die formed on a silicon wafer, is provided. The system includes a two dimensional inspection system that can locate one or more features, such as bump contacts on the die, and which can also generate feature coordinate data. The system also includes a three dimensional inspection system that is connected to the two dimensional inspection system, such as through an operating system of a processor. The three dimensional inspection system receives the feature coordinate data and generates inspection control data.

18 Claims, 6 Drawing Sheets

SYSTEM AND METHOD FOR INSPECTING BUMPED WAFERS

FIELD OF THE INVENTION

The present invention pertains to the field of image data processing. More specifically, the invention relates to a system and method for inspecting bumped wafers that uses data from a two-dimensional image data analysis to perform a three-dimensional image data analysis.

BACKGROUND

Image data processing is used to inspect items during and after the manufacturing process. Such image data is typically gathered using a digital camera or other device that digitizes image data within the focal field of the device. The digitized image data is then analyzed, either manually or by software systems or other digital systems.

In cases where the image data is more complex, it is often necessary to manually review the image data before software systems can be used. For example, image data of dies that have been formed on a silicon wafer may be inspected by software systems. Nevertheless, areas of the die may have to be manually selected that cannot be analyzed by the software systems, such as areas that require three-dimensional analysis. Such three-dimensional analysis can require placing a three-dimensional sensing component, such as a laser track, on features of the component. Image data from the feature, as illuminated by the three-dimensional sensing component, is then analyzed so as to determine the coordinates in three dimensions of the illuminated feature.

Although analysis of image data by software systems is useful, the manual selection of features from which to obtain image data can be the largest time component of the inspection process. As a result, the three-dimensional inspection of features of components can be time-consuming and require operator resources. Furthermore, operator-assisted inspection can result in high levels of mistakes, such as missed features, improperly illuminated features, or other problems.

SUMMARY OF THE INVENTION

In accordance with the present invention, a system and method for inspecting components are provided that overcome known problems with inspecting components.

In particular, a system and method for inspecting components are provided that uses two-dimensional inspection data to locate features by which to control the three-dimensional inspection of the component.

In accordance with an exemplary embodiment of the present invention, a system for inspecting a component is provided, such as a die cut from a silicon wafer. The system includes a two dimensional inspection system that can locate features on the component, such as bump contacts. The two dimensional inspection system can generate feature coordinate data for the located features. A three dimensional inspection system is connected to the two-dimensional inspection system. The three dimensional inspection system receives the feature coordinate data from the two dimensional inspection system, and generates inspection control data, such as data for controlling the placement of a laser track. The three dimensional inspection system then inspects the component after generating the inspection control data.

The present invention provides many important technical advantages. One important technical advantage of the present invention is a system and method for inspecting a component that uses feature coordinate data from a two-dimensional inspection to perform a three-dimensional inspection. The present invention thus combines two-dimensional inspection techniques with three-dimensional inspection techniques in a manner that allows three-dimensional inspection control data to be determined without operator input.

Those skilled in the art will further appreciate the advantages and superior features of the invention together with other important aspects thereof on reading the detailed description that follows inconjunction with the drawings.

DETAILED DESCRIPTION OF PREFERRED EMBODIMENTS

Figure 1:
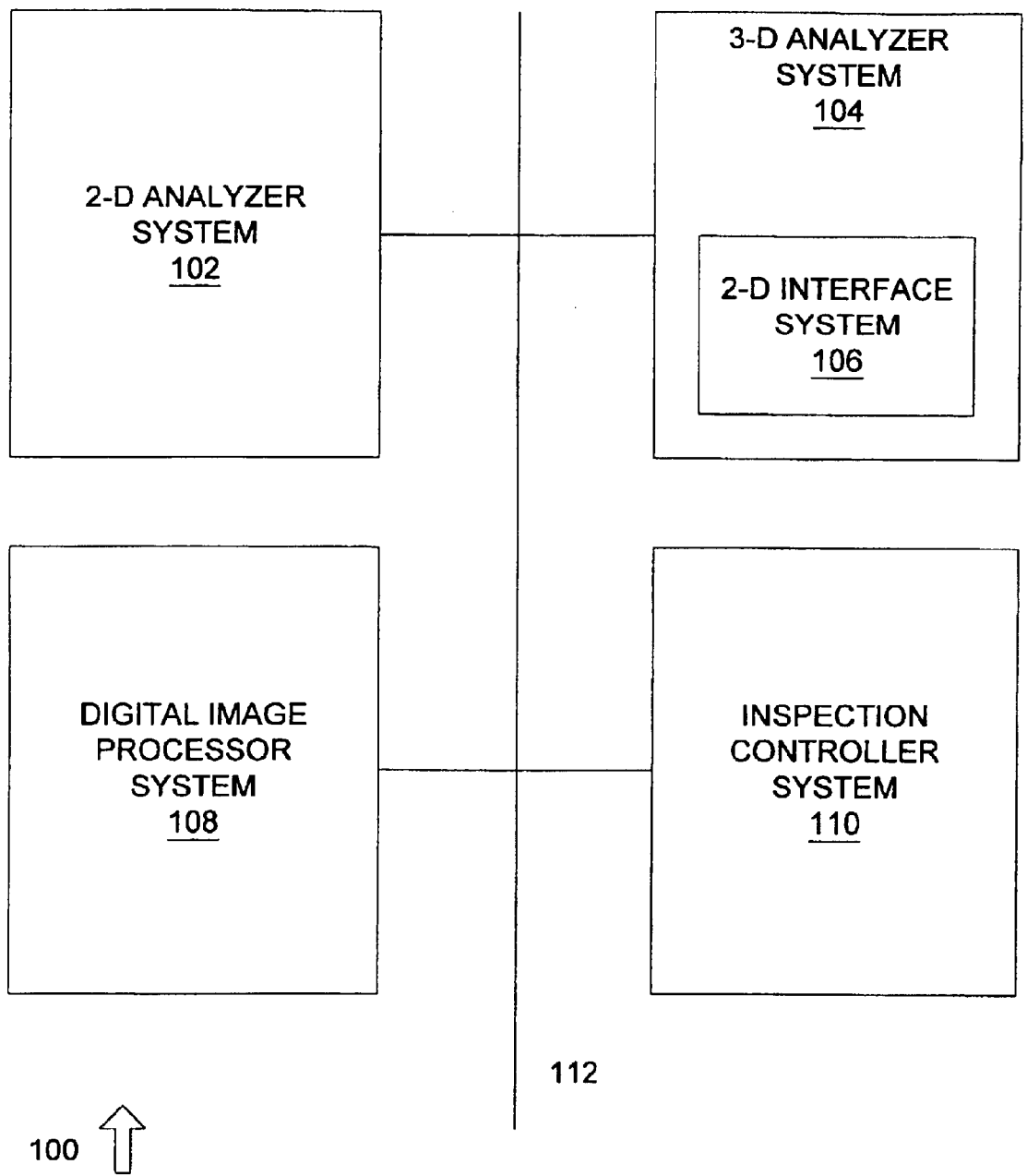
FIG. 1 is a diagram of a system for processing image data in accordance with an exemplary embodiment of the present invention.

In the description which follows, like parts are marked throughout the specification and drawings with the same reference numerals, respectively. The drawing figures may not be to scale and certain components can be shown in generalized or schematic form and identified by commercial designations in the interest of clarity and conciseness.

FIG. 1 is a diagram of a system 100 for processing image data in accordance with an exemplary embodiment of the present invention. System 100 can be used to perform three-dimensional image analysis of image data based upon the results of a two-dimensional image analysis, and can generate inspection control data to control the placement of the component during inspection.

System 100 includes two-dimensional analyzer system 102, which can be implemented in hardware, software, or a suitable combination of hardware and software, and which can be one or more software systems operating on a processor of a WAV-1000 Wafer Inspection System, available from Semiconductor Technologies and Instruments of Plano, Tex. As used herein, a software system can include one or more lines of code, objects, agents, subroutines, separate software programs, two or more lines of code operating in two or more separate software programs, or other suitable software architectures. In one exemplary embodiment, a software system includes one or more lines of code operating in a general purpose software application, such as an operating system, and one or more lines of code operating in a specific purpose software application.

Two-dimensional analyzer system 102 is coupled to digital image processor system 108 through communications medium 112. As used herein, the term "couple" and its cognate term such as "couples" and "coupled" can include a physical connection (such as through a copper conductor), a virtual connection (such as through randomly assigned memory locations of a data memory device), a logical connection (such as through logical gates of a semiconducting device), other suitable connections, or suitable combinations of such connections. In one exemplary embodiment, systems or components are coupled to other systems or components through intervening systems or components, such as through an operating system of a computing platform.

Two-dimensional analyzer system 102 receives digital image data from digital image processor system 108. Digital image processor system 108 can include one or more digital imaging devices, such as digital cameras or digital scanners, which receive image data from a field of view and convert the image data into digitized data. In one exemplary embodiment, digital imager processor system 108 converts digital image data into an N×M picture element ("pixel") array, where each pixel includes brightness data varying from a minimum to a maximum value, such as from 0 to 255. Digital image processor system 108 receives the image data and converts the image data into a data having a predetermined format. This data is provided to two-dimensional analyzer system 102, which can analyze the data to locate one or more features.

For example, two-dimensional analyzer system 102 can use feature identification procedures to locate one or more features on the component, such as a silicon wafer having bump contacts. The coordinate data for the location of each of the bumps is then provided by two-dimensional analyzer system 102 to three-dimensional analyzer system 104, which uses the coordinate data to determine an optimal inspection sequence for performing the three-dimensional inspection.

Three-dimensional analyzer system 104 can be implemented in hardware, software, or a suitable combination of hardware and software, and can be a software system operating on a processor of the WAV-1000 Wafer Inspection System. Three-dimensional analyzer system 104 receives coordinate data from two-dimensional analyzer system 102 that identifies the coordinates of the one or more image features. For example, three-dimensional analyzer system 104 can receive coordinate data for a plurality of bumps on a bumped wafer from two-dimensional analyzer system 102. Three-dimensional analyzer system 104 then determines the inspection sequence for performing a three-dimensional inspection of the component. In one exemplary embodiment, the three-dimensional inspection of the component is performed by placing a laser track (such as is formed by tracing a laser beam back and forth repeatedly over a track having a predetermined length) over the one or more features. Pixel data is then generated and the shape of the laser track is then analyzed. The laser track will draw a straight line when placed on a flat surface. Areas over which the surface is not flat will create variations in the otherwise linear laser track. Three-dimensional analyzer system 104 receives image data from digital image processor system 108 when the laser track is placed on the component, and analyzes the image data to determine the three dimensional characteristics of any features that the laser track is placed on.

Three-dimensional analyzer system includes two-dimensional interface system 106, which can be implemented in hardware, software, or a suitable combination of hardware and software. Two-dimensional interface system 106 receives the coordinate data for the one or more features from two-dimensional analyzer system 102 and provides the coordinate data to three-dimensional analyzer system 104. Three-dimensional analyzer system 104 then determines an inspection sequence for the component, such as a sequence of component movements that will allow all of the features to be placed under the laser inspection track or other suitable three dimensional inspection devices. Three-dimensional analyzer system 104 also generates data that can be used to control the location of the component that will be inspected. For example, if the laser track were fixed then it would be necessary to move the component so that all features of the component are illuminated by the laser track in order to perform the inspection.

Inspection controller system 110 is coupled to three-dimensional analyzer system 104 through communications medium 112, and receives the component placement control data from three-dimensional analyzer system 104. Inspection controller system 110 can be implemented in hardware, software, or a suitable combination of hardware and software, and can be a wafer table position controller that includes one or more servo motors or other electromechanical devices that are used to control the position of a wafer inspection table. Inspection controller system 110 can control the placement of the component that is being inspected so that three-dimensional analyzer system 104 can obtain digital image data for processing to determine the three dimensional characteristics of the features of the component.

Communications medium 112 is used to allow two-dimensional analyzer system 102, three-dimensional analyzer system 104, digital image processor system 108, and inspection controller system 110 to interface.

Communications medium 112 can be an operating system of the processor of the WAV-1000 Wafer Inspection System, other operating systems, a data bus, or other suitable communications media.

In operation, system 100 allows a component to be inspected using three-dimensional image analysis based upon feature data that is obtained from two-dimensional image data analysis. The two-dimensional image data analysis is analyzed to identify one or more features of the component, and the component coordinate data is then provided to three-dimensional analyzer system 104. Three-dimensional analyzer system 104 then determines the optimal placement and inspection procedure for inspecting the component for three-dimensional features. Three-dimensional analyzer system 104 can also generate component movement control data so that the component is moved as needed in order to perform the three-dimensional analysis.

Figure 2:
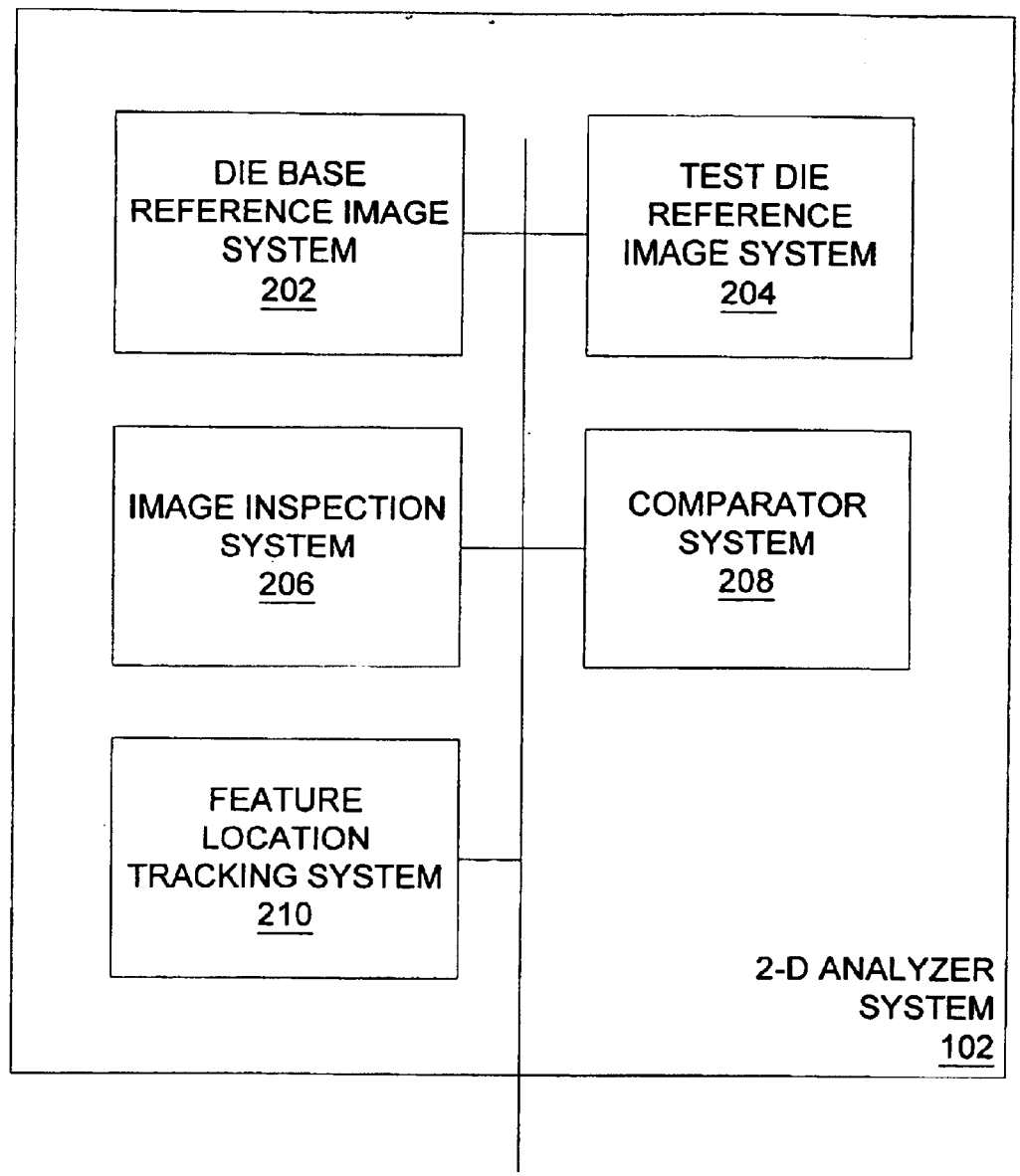
FIG. 2 is a diagram of a system for performing two-dimensional image data analysis in accordance with exemplary embodiment of the present invention.

FIG. 2 is a diagram of a system 200 for performing two-dimensional image data analysis in accordance with an exemplary embodiment of the present invention. System 200 includes two-dimensional analyzer system 102 and additional functionality that allows coordinate data for a plurality of features to be identified and provided to three-dimensional analyzer system 104.

System 200 includes die-based reference image system 202, test die reference image system 204, image inspection system 206, comparator system 208 and feature location tracking system 210, each of which can be implemented in hardware, software, or a suitable combination of hardware and software, and which can be one or more software systems operating on a processor of a WAV-1000 Wafer Inspection System. Die-based reference image system 202 includes die-based reference image data that is gathered from a die prior to the installation of one or more features on the die. For example, the, die, can be provided with one or more bumped wafer contacts that are used to connect an integrated circuit on the die to other devices. Die-based reference image system 202 can be used to store an image of the die prior to installation of the contact bumps for use as the reference image for inspection. In this manner, two different images of the component can be used to help detect features of the component that might otherwise be difficult to detect.

Test die reference image system 204 can include one or more test die reference images that are generated from the final component, reference components, or other suitable components. Test die reference image system 204 can include test die images that are provided by an operator from one or more finished dies, test die images that are assembled from portions of one or more finished dies, or other suitable test die reference images.

Image inspection system 206 can receive image inspection data from digital image processor system 108 or other suitable digital image data systems, and can provide the image inspection data to comparator system 208 for analysis. The image inspection data stored in image inspection system 206 is digitally encoded data that is representative of the image of the component that is being inspected.

Comparator system 208 receives the image inspection data from image inspection system 206 in addition to the reference image data from either die-based reference image system 202 or test die reference image system 204, and generates feature location data based upon the difference in the picture element brightness data. For example, comparator system 208 can receive an N×M matrix of pixel brightness data from die-based reference image system 202 or test die reference image system 204, and can subtract the brightness values of each pixel of the N×M matrix from the brightness values of each pixel of the N×M matrix received from image inspection system 206. In this manner, comparator system 208 generates an N×M matrix of pixels of difference image data, where a pixel has a non-zero, brightness value if there is a difference between the pixel brightness value in the test inspection image and the corresponding pixel brightness value in the reference image. Comparator system 208 can also analyze the difference image data to locate one or more features in the image data, such as by locating groups of pixels in the N×M matrix of the brightness data that have values greater than a predetermined value and a predetermined configuration.

Feature location tracking system 210 is coupled to comparator system 208 and receives feature coordinate data after the features are located by comparator system 208. For example, feature location tracking system 210 can receive the coordinate data for each feature of a component as it is found, and can store the coordinate data in a predetermined database. Feature location tracking system 210 can also determine whether all features of the component have been found based upon an operator-entered number of features or other suitable data.

In operation, system 200 is used to analyze two-dimensional digital image data to locate one or more features. Coordinate data identifying the location of each feature is then stored, such as for subsequent provision to a three-dimensional image data analysis system. System 200 allows a reference image to be used that is made on the same or a representative component prior to the installation of the features that are being detected, so as to allow such features to be more readily detected. Other suitable reference images can also be used.

Figure 3:
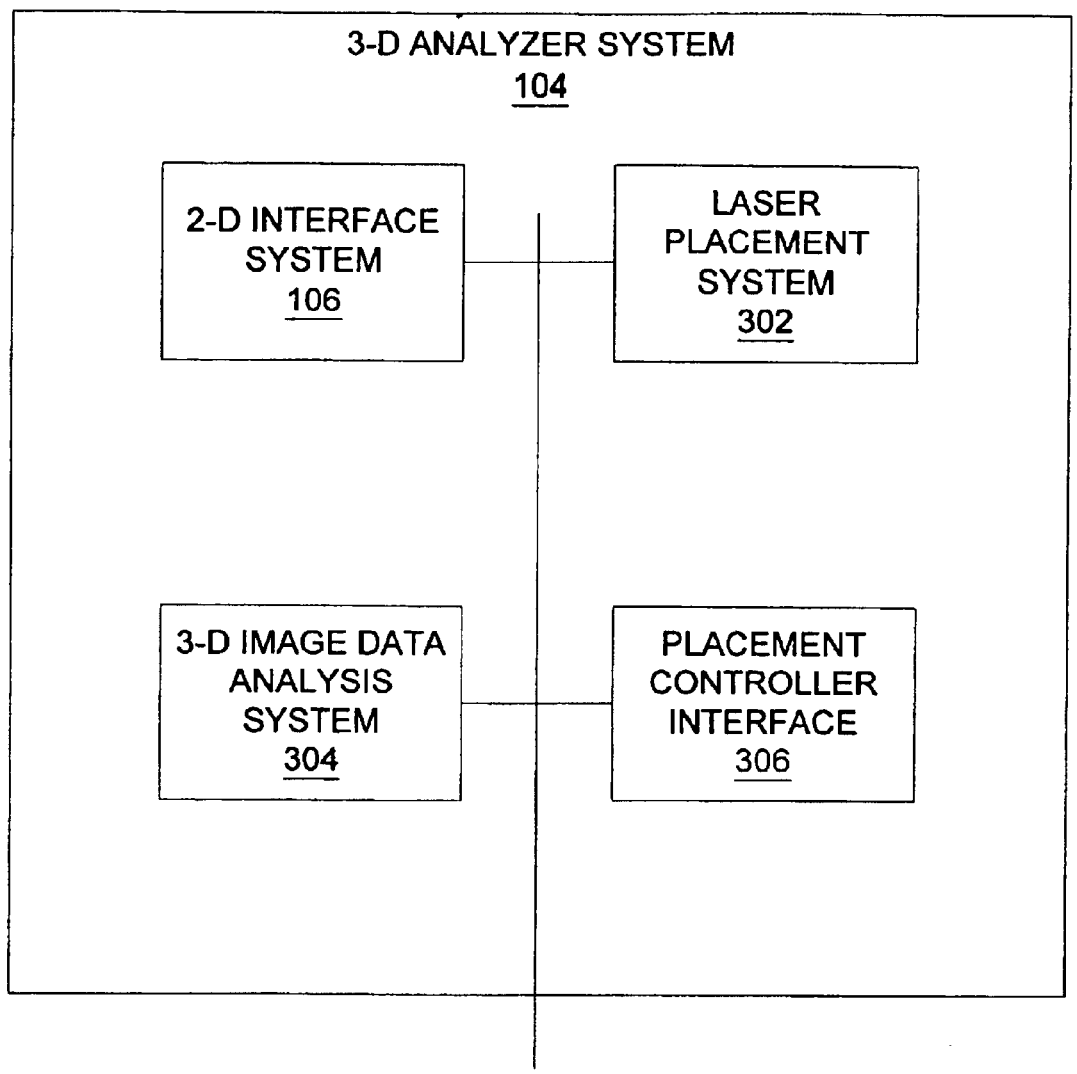
FIG. 3 is a diagram of a system for performing a three-dimensional image data analysis in accordance with an exemplary embodiment of the present invention.
Figure 3:

FIG. 3 is a diagram of a system 300 for performing three-dimensional image data analysis in accordance with an exemplary embodiment of the present invention. System 300 includes three-dimensional analyzer system 104 and additional functionality.

System 300 includes laser placement system 302, three-dimensional image data analysis system 304, and placement controller interface 306, each of which can be implemented in hardware, software, or a suitable combination of hardware and software, and which can be software systems operating on the WAV-1000 Wafer Inspection System. Laser placement system 302 receives feature coordinate data from two-dimensional interface system 106 and determines an optimal placement for a laser track such that each of the features is illuminated by the laser track at least once. Laser placement system 302 also generates component movement control data that is used to control the position of the component so that the laser track placement can be accomplished.

Three-dimensional image data analysis system 304 receives digital image data that includes one or more features that have been illuminated by a laser track and determines the three-dimensional coordinates of the features. For example, if the laser track is lying on a flat surface, the line formed by the laser track can be straight. For features that lie above the surface, then the line formed by the laser track can deviate away from the angle of viewing. For features that lie below the surface, the line formed by the laser track can deviate towards the field of viewing. Multiple fields of viewing can also be used to provide a better estimate of the three-dimensional coordinates of the feature.

Placement controller interface 306 receives the component movement control data from laser placement system 302 and interfaces with an inspection controller system 110 so as to control the placement of the component that is being inspected. For example, placement controller interface 306 can provide control commands to the inspection controller system 110 in response to data received from three-dimensional image data analysis system 304 that indicates whether analysis of the image data created from the current placement of the laser track has been completed. Placement controller interface system 306 can then transmit the next coordinates for the component to be moved to.

In operation, system 300 is used to perform a three dimensional analysis of a component to locate the position and size of three-dimensional features. System 300 uses feature coordinate data from a two dimensional analyzer system to determine optimal placement of three dimensional analysis components, such as laser tracks. In this manner, system 300 allows a piece to be inspected for three-dimensional data without operator intervention after the two dimensional analysis.

Figure 4:
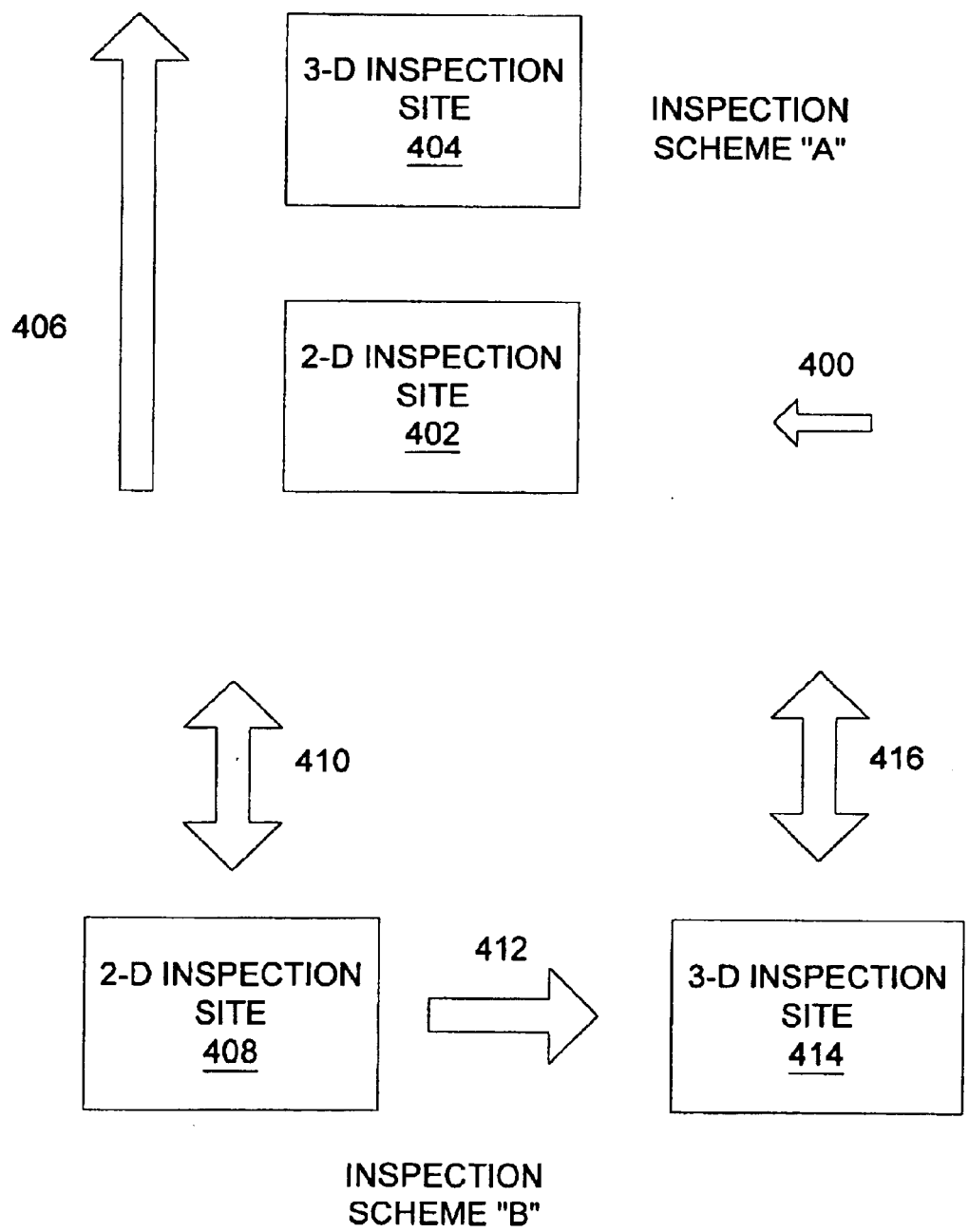
FIG. 4 is a diagram of two exemplary inspection schemes in accordance with an exemplary embodiment of the present invention.

FIG. 4 is a diagram 400 of two exemplary inspection schemes in accordance with an exemplary embodiment of the present invention. Diagram 400 includes inspection scheme A and inspection scheme B.

Inspection scheme A provides for a first two-dimensional inspection site 402, which occurs before the second three-dimensional inspection site 404. The direction of inspection is thus in the direction of arrow 406. As a component is moved in the direction of arrow 406, it crosses two-dimensional inspection site 402 first, and then proceeds to three-dimensional inspection site 404. In this manner, data received from two-dimensional inspection site 402 can be used to perform the inspection at three-dimensional inspection site 404. One drawback of inspection scheme A is that inspection can only proceed in the direction of arrow 406. Thus, if the components are placed in rows and columns, such as in the case of dies formed on a silicon wafer, then two-dimensional inspection site 402 must be moved back to the beginning of each row in order to begin inspection of that row.

In contrast, inspection scheme B provides for a two-dimensional inspection to take place at two-dimensional inspection site 408 in the direction shown by arrow 410 and then for a three-dimensional inspection to take place at three-dimensional inspection site 414 in the direction of arrow 416. The component is moved after being placed in two-dimensional inspection site 408 in the direction of arrow 412. Thus, if components are arranged in rows and columns, then they can be inspected at two-dimensional inspection site 408 first, and then a three-dimensional inspection can be performed at three-dimensional inspection site 414 on each component using the data gathered from the two-dimensional inspection. In this manner, component inspection can proceed in either direction such that the silicon wafer or other inspection platform does not have to be returned to the same side at the beginning of a new row. This configuration can provide a timesaving element so as to increase the total volume of components inspected per unit time.

Figure 5:
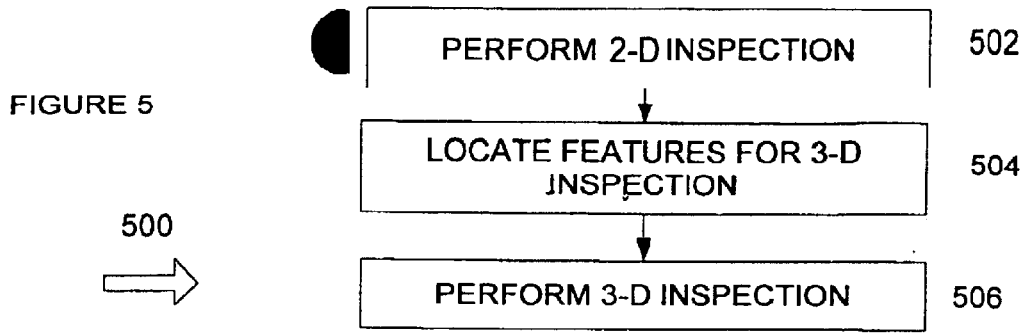
FIG. 5 is a diagram of a method for inspecting components in accordance with an exemplary embodiment of the present invention.

FIG. 5 is a diagram of a method 500 for inspecting components in accordance with an exemplary embodiment of the present invention. Method 500 begins at 502 where a two dimensional inspection is performed. For example, the two dimensional inspection can be performed by subtracting pixel brightness data of an N×M reference image from pixel brightness data of an N×M test image to create an N×M difference image.

After performing the two-dimensional inspection at 502 the method proceeds to 504 where features for the three-dimensional inspection are located. For example, the features may include bumped contact points for a silicon wafer, where the placement of a three-dimensional inspection tool relative to the inspected object can be optimized based a upon on the location of the bumps. The location of the features, placement of inspection tools, and movement of the component are determined at 504 and the method proceeds to 506.

At 506, a three-dimensional inspection is performed of the component. For example, the three-dimensional inspection can be performed by placing a laser track on one or more features of the component, storing image data that includes the component illuminated by the laser track, and then analyzing the image data that is generated during the time that the laser track was illuminating the component. The laser track will be linear over flat portions of the component, and will deviate from linearity when placed over raised or lowered features. Such variations from linearity can be used to determine the height or depth of a feature on a component.

In operation, method 500 is used to perform a three dimensional inspection of a component without operator intervention. The coordinate data for the features that are being inspected for the three-dimensional inspection are determined from a two-dimensional inspection, thus eliminating the need for an operator to identify the features prior to the three-dimensional inspection. Method 500 thus provides for a faster three-dimensional inspection and also provides for increased accuracy and reliability of feature identification.

Figure 6:
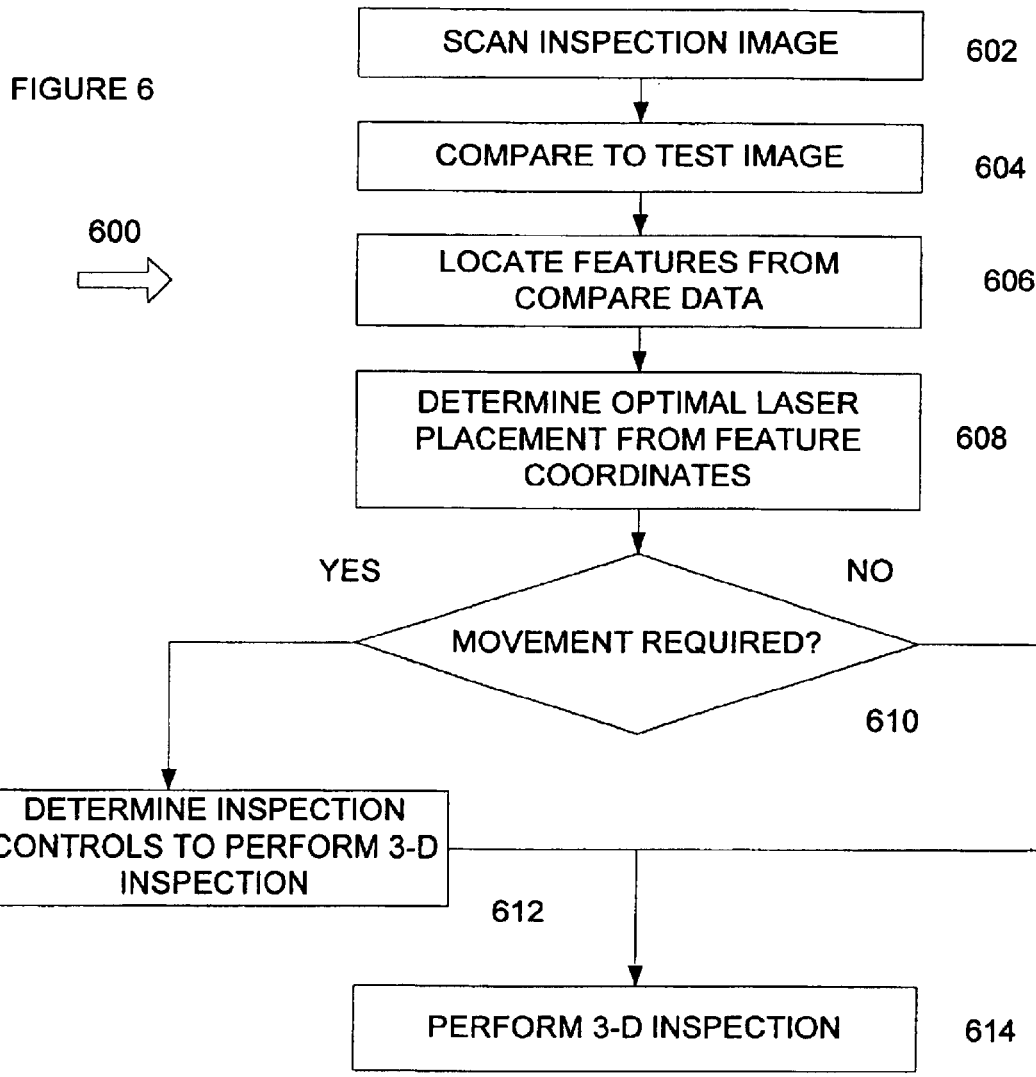
FIG. 6 is a diagram of a method for performing a two-dimensional and three-dimensional inspection of a component in accordance with an exemplary embodiment of the present invention.

FIG. 6 is a diagram of a method 600 for performing a two-dimensional and three-dimensional inspection of a component in accordance with an exemplary embodiment of the present invention. Method 600 begins at 602 where an inspection image is scanned. For example, a silicon wafer having a plurality of dies formed on it can be inspected. The field of inspection can be the size of one or more die formed on the silicon wafer, such that each inspection image includes at least one die. This inspection image is scanned at 602 and method proceeds to 604.

At 604, the inspection image is compared to the test image. For example, a test image can be obtained by scanning an image of the component prior to performing a manufacturing step, such as the installation of wafer bumps. Likewise, a test image can be obtained by using reference images that do not have nonconforming features, or by other suitable procedures. The inspection image is then compared to the test image, such as by subtracting pixel brightness data from corresponding pixels of an N×M matrix of the inspection image and the test image. The method then proceeds to 606.

At 606, features are located from the compare data. For example, when the compare data includes an N×M pixel array of difference data, the difference data can be inspected for random variations, lines, circles, or other figures, and image data processing techniques can be used to locate groups of pixels that have the same form as known predetermined features. These features are detected by this or other suitable methods at 606 and the method proceeds to 608. At 608, the optimal placement of a laser track is determined from the feature coordinates. For example, if a silicon wafer having contact bumps is being inspected, it may be determined that the laser track can be placed over all contact bumps by rotating the silicon wafer 90° four times, such as when the bumps lie along a rectangular outline of the wafer. In this exemplary embodiment, each contact bump can be illuminated at least once by this laser track placement sequence. Likewise, other suitable placement sequences can also be determined. The method then proceeds to 610.

At 610, it is determined whether movement is required in order to perform the three-dimensional inspection. For example, in the previous example it would be required to move the component 90° in rotation and perhaps to perform additional X and Y-axis movements. Movement of the device that generates the laser track or other suitable movement can also be performed.

If it is determined at 610 that movement is required, the method proceeds to 612 where inspection controls are generated. For example, inspection controls can include controls that translate in English as "rotate piece 90° around coordinates [0,0], and then shift component by coordinates [−10,10]." If it is determined at 610 that movement is not required the method proceeds to 614. At 614, three-dimensional inspection is performed, such as by a single placement of the laser track, multiple placements of laser track, or other suitable procedures. Image data generated during each placement of the laser track, or other suitable procedures, are then stored and analyzed to determine the location and size of various features.

In operation, method 600 is used to perform a three-dimensional inspection of a component, based on data that has been obtained from a two-dimensional inspection of the component. In this manner, operator intervention to identify features is not required, thus facilitating the inspection process by allowing it to proceed more quickly and by ensuring that features are not inadvertently overlooked by an operator.

Figure 7:
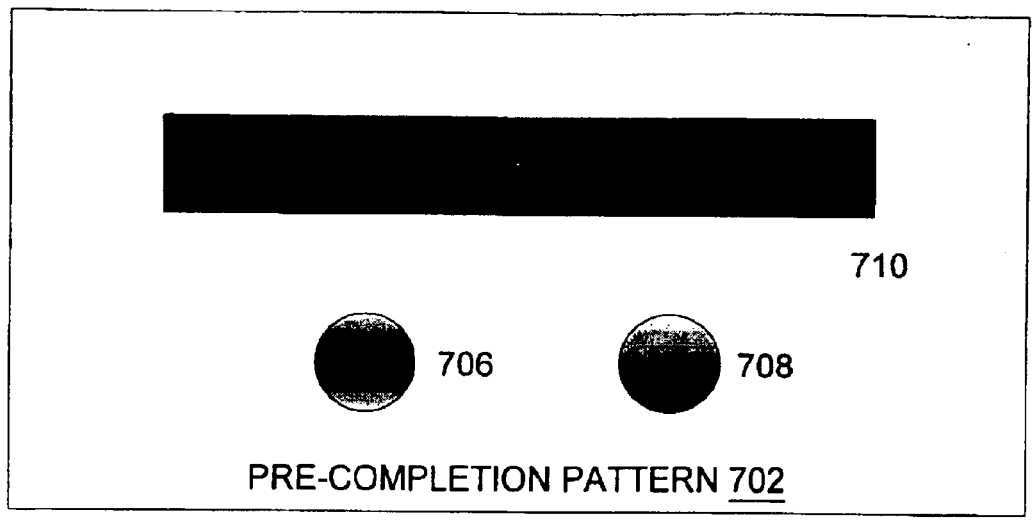
FIG. 7 is a diagram of two exemplary image data sets in accordance with an exemplary embodiment of the present invention.
Figure 7:
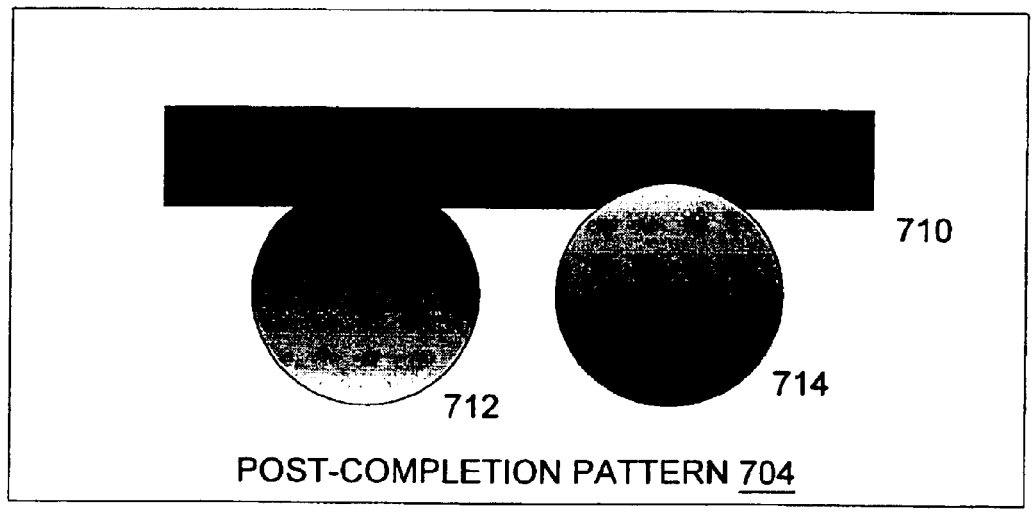

FIG. 7 is a diagram 700 of two exemplary image data sets in accordance with an exemplary embodiment of the present invention. Diagram 700 can be used to illustrate features of a die-based reference image process and a test die reference image process.

Diagram 700 includes pre-completion pattern 702 and post completion pattern 704, which are representations of N×M digital data sets of a portion of a silicon wafer die prior to the installation of two bump contacts and after the installation of the two bump contacts. Deposition sites 706 and 708 of pre-completion pattern 702 are the locations where the bump contacts will be placed, and can be surface manifestations of underlying metallic or semiconducting material that is used to form an electrical contact with a circuit that has been formed on the silicon wafer. Region 710 is a region of material that has an optical appearance that is similar in pixel brightness value to that of the deposition sites 706 and 708. The spatial separation of deposition sites 706 and 708 and region 710 would allow conventional image data analysis techniques to be used to locate the edges of each of the three features.

Post-completion pattern 704 includes bump contacts 712 and 714, which extend into region 710. Although bump contacts 712 and 714 might be able to be detected apart from region 710, the similarity in pixel gradient values between region 710 and bump contacts 712 and 714 could result in an incorrect determination of the edge of bump contacts 712 and 714 if the digital data that comprises post-completion pattern 704 were analyzed by known image data analysis techniques.

In one exemplary embodiment of the present invention, an N×M pixel array of difference image data is created by subtracting the N×M pixel array of brightness data of post-completion pattern 704 from the N×M pixel array of brightness data of pre-completion pattern 702. The difference data can then be analyzed to detect the edges of bump contacts 712 and 714. This procedure minimizes the effect of region 710 on the image of bump contacts 712 and 714.

In another exemplary embodiment of the present invention, an N×M pixel array of difference image data is created from operator-selected portions of the N×M pixel array of brightness data of post-completion pattern 704. In this exemplary embodiment, an operator can select bump contact 714 as a model for bump contact image data. In this manner, each of the bump contacts of the reference image would be optimized so that the effect of region 710 could be minimized.

In operation, diagram 700 illustrates features of the present invention that allow reference image data to be generated from image data of an inspection component before completion of assembly processes, and after completion of the assembly process. In this manner, reference image data can be created for use in generating difference data, such that features of a component can be readily detected by image data analysis.

Although preferred and, exemplary embodiments of a system and method for inspecting bumped wafers have been described in detail herein, those skilled in the art will also recognize that various substitutions and modifications can be made to the systems and methods without departing from the scope and spirit of the appended claims.

What is claimed is:

1. A system for inspecting a component comprising:
   a two dimensional inspection system locating a plurality of feature on the component and generating feature coordinate data; and
   a three dimensional inspection system coupled to the two dimensional inspection system, the three dimensional inspection system receiving the feature coordinate data and generating inspection control data.

2. The system of claim 1 further comprising a component inspection controller coupled to the three dimensional inspection system, the component inspection controller receiving the inspecting control data and controlling the location of the component based upon the inspection control data.

3. The system of claim 1 further comprising:
   a reference image system storm& one or more reference images;
   a test image system storing test image data; and
   a comparator system coupled to the reference image system and the test image system, the comparator system generating difference data from the reference image data and the test image data.

4. The system of claim 3 wherein the reference image system comprises a die base reference image system storing image data of a die prior to installation of bumps.

5. The system of claim 3 wherein the reference image system comprises a test die reference image system storing image data of a test die with installed bumps.

6. The system of claim 1 wherein the two dimensional inspection system further comprises a feature location tracking system storing the feature location data and providing the feature location data to the three dimensional inspection system after all features of the component are located.

7. The system of claim 1 wherein the three dimensional inspection system further comprises a laser placement system that determines the location of a laser inspection track on the component from the feature location data.

8. The system of claim 1 wherein the three dimensional inspection system further comprises a three dimensional image data analysis system that receives laser image data and determines three dimensional feature location data from the laser image data.

9. A method for inspecting a component comprising:
   processing two dimensional image data of the component to determine location data for each of a plurality of features on the component;
   determining control data for a three dimensional inspection of the component from the location data for each of the plurality of features; and
   performing a three dimensional inspection of the component using the control data.

10. The method of claim 9 wherein processing the two dimensional image data of the component to determine the location data for each of the plurality of features on the component comprises:
    comparing test image data to die base reference image data to generate difference data; and
    analyzing the difference data to determine the location of each of the plurality of features.

11. The method of claim 9 wherein processing the two dimensional image data of the component to determine the location data for each of the plurality of features on the component comprises:
    comparing test image data to test die reference image data to generate difference data; and
    analyzing the difference data to determine the location of each of the plurality of features.

12. The method of claim 9 wherein determining the control data for the three dimensional inspection of the component from the location data for each of the plurality of features comprises:

determining placement sequence data for a laser inspection track such that the laser inspection track is placed on each of the plurality of features at least once; and determining component movement control data from the placement sequence data.

13. The method of claim 9 wherein performing the three dimensional inspection of the component using be control data comprises:

obtaining image data from a laser inspection track on the component; and analyzing the image data to determine the location of one or more features.

14. The method of claim 13 further comprising moving the component until the image data has been obtained for each of the features on the component.

15. The method of claim 13 further comprising generating error data if the location of any of the one or more features is outside of a predetermined location range.

16. A method for processing image data to locate one or more features comprising:

receiving first image data of a component prior to installation of one or more features:

receiving second image data of the component after the installation of the one or more features;

comparing the first image data and the second image data to generate difference data;

determine the location of each of the one or more features from the difference data; and determining the placement of a three-dimensional inspection component based upon the location of each of the one or more features.

17. The method of claim 16 wherein determining the placement of the three-dimensional inspection component comprises determining the location of a laser track.

18. A method for processing image data to locate one or more features comprising:

receiving first image data of a component prior to installation of one or more features;

receiving second image data of the component after the installation of the one or more features;

comparing the first image data and the second image data to generate difference data;

determining the location of each of the one or more features from the difference data; and wherein determining the location of each of the one or more features from the difference data comprises using the difference data to locate an edge of one or more of the features in locations where a value of brightness data of an area in the first image data is close to a value of brightness data of an area in the second image corresponding to one of the features.

\* \* \* \* \*